(12) United States Patent
Britt et al.

(10) Patent No.: US 6,718,979 B1
(45) Date of Patent: Apr. 13, 2004

(54) OXYGEN MASK ASSEMBLY

(75) Inventors: Danny Britt, Jackson, TN (US); Michael Henigman, Costa Mesa, CA (US); Kurt Meyer, Arlington Heights, IL (US)

(73) Assignee: DHD Healthcare Corporation, Wampsville, NY (US)

( * ) Notice: Subject to any disclaimer, the term of this patent is extended or adjusted under 35 U.S.C. 154(b) by 33 days.

(21) Appl. No.: 09/588,164

(22) Filed: Jun. 5, 2000

(51) Int. Cl.[7] .................................................. A62B 7/00
(52) U.S. Cl. ............................. 128/205.11; 128/206.21; 128/203.25; 128/204.22; 128/204.25; 128/205.24
(58) Field of Search ..................... 128/205.11, 206.21, 128/206.26, 203.25, 204.22, 204.24, 204.25, 205.24, 207.12

(56) References Cited

U.S. PATENT DOCUMENTS

| | | |
|---|---|---|
| 1,630,501 A | 5/1927 | Steese |
| 2,547,458 A | 4/1951 | Goodner ...................... 128/203 |
| 3,189,027 A | 6/1965 | Bartlett, Jr. ................. 128/142 |
| 3,610,237 A | 10/1971 | Barkalow et al. ......... 128/145.8 |
| 3,714,944 A * | 2/1973 | Price et al. ............. 128/203.12 |
| 3,726,274 A | 4/1973 | Bird et al. ................ 128/145.8 |
| 3,794,072 A * | 2/1974 | Diedrich et al. ............ 137/604 |
| 3,826,255 A | 7/1974 | Havstad et al. .............. 128/194 |
| 3,830,257 A * | 8/1974 | Metivier ................. 137/625.41 |
| 3,906,996 A * | 9/1975 | DePass et al. ............... 137/604 |
| 3,913,607 A | 10/1975 | Price ........................... 137/271 |
| 3,977,432 A | 8/1976 | Vidal ........................... 137/604 |
| 4,036,253 A | 7/1977 | Fegan et al. ................. 137/556 |
| 4,682,591 A | 7/1987 | Jones ....................... 128/204.25 |
| 4,702,240 A * | 10/1987 | Chaoui ..................... 128/204.18 |
| 4,848,333 A | 7/1989 | Waite ...................... 128/205.11 |
| 4,905,688 A | 3/1990 | Vicenzi et al. .......... 128/204.21 |
| 4,919,132 A | 4/1990 | Miser ....................... 128/205.17 |
| 5,301,662 A * | 4/1994 | Bagwell et al. ......... 128/200.14 |
| 5,372,129 A * | 12/1994 | Ryder ...................... 128/205.11 |
| 5,425,358 A * | 6/1995 | McGrail et al. .......... 128/205.24 |
| 5,460,174 A | 10/1995 | Chang ..................... 128/204.25 |
| 5,479,920 A * | 1/1996 | Piper et al. ............. 128/204.23 |
| RE35,339 E * | 10/1996 | Rapoport ................. 128/204.18 |
| 5,645,055 A | 7/1997 | Danon ..................... 128/204.25 |
| 5,660,174 A * | 8/1997 | Jacobelli ................. 128/206.24 |
| 5,682,874 A * | 11/1997 | Grabenkort et al. ..... 128/200.14 |
| 5,690,097 A * | 11/1997 | Howard et al. .......... 128/205.11 |
| 5,701,886 A * | 12/1997 | Ryatt ...................... 128/203.12 |
| 5,797,389 A * | 8/1998 | Ryder ...................... 128/200.21 |
| 5,937,851 A * | 8/1999 | Serowski et al. ........ 128/202.27 |
| 6,189,531 B1 * | 2/2001 | Tatarek ................... 128/205.24 |

* cited by examiner

*Primary Examiner*—Weilun Lo
*Assistant Examiner*—Darwin P Erezo
(74) *Attorney, Agent, or Firm*—August E. Roehrig, Jr.; Hancock & Estabrook, LLP

(57) ABSTRACT

An oxygen mask assembly including an oxygen dilutor assembly with air inlet apertures located in a top wall thereof for diluting the oxygen flowing therethrough. In one embodiment, the mask assembly additionally includes an air reservoir bag assembly, a one-way inhalation valve for maintaining continuous positive airway pressure in the mask and a pressure valve on the mask for adjusting the air pressure in the mask.

24 Claims, 5 Drawing Sheets

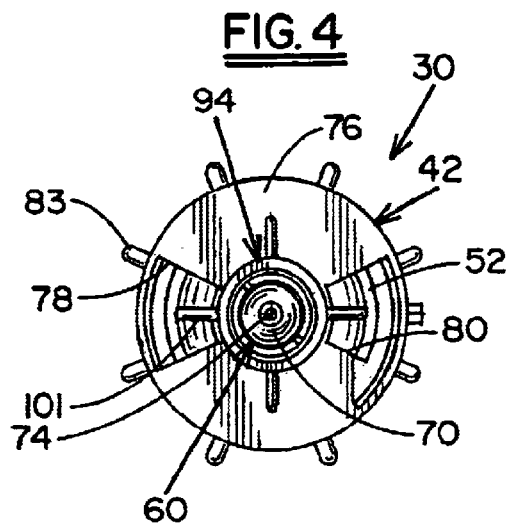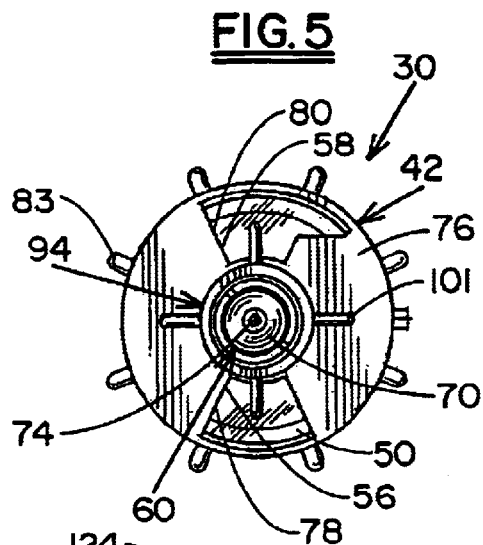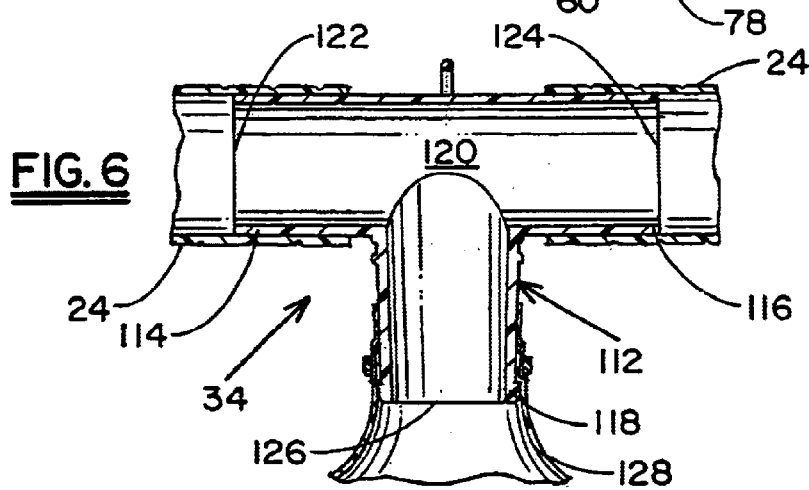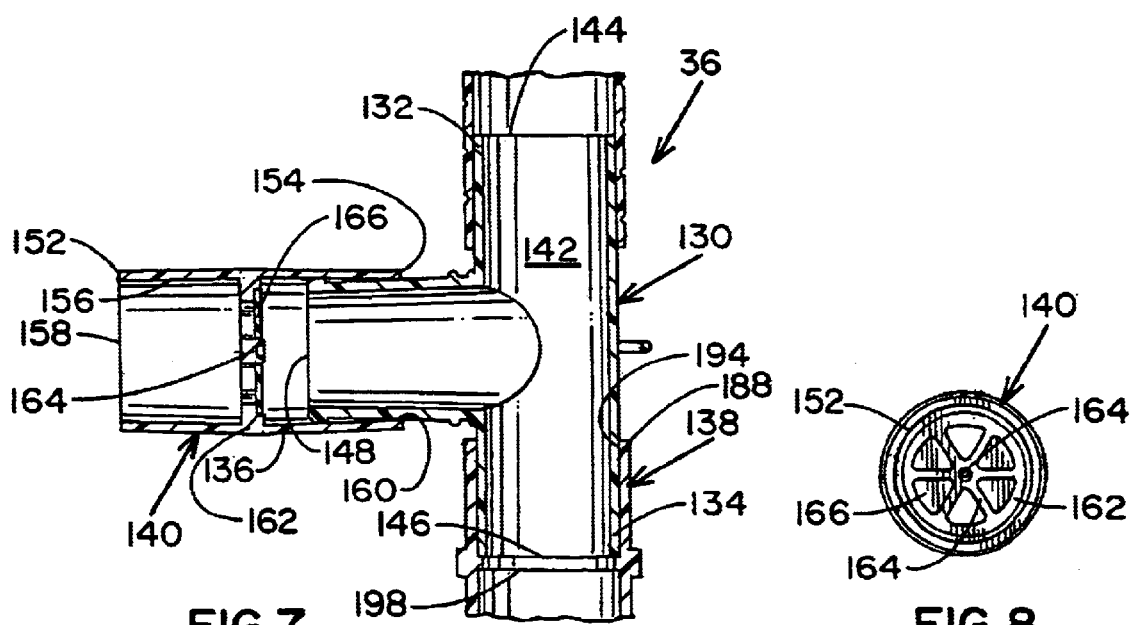

OXYGEN MASK ASSEMBLY

FIELD OF THE INVENTION

This invention relates to an oxygen mask assembly and, more particularly, to an oxygen mask assembly incorporating an improved oxygen dilutor assembly.

BACKGROUND OF THE INVENTION

While routinely used in the intensive care setting, the use of noninvasive continuous positive airway pressure (CPAP) oxygen mask assemblies has experienced increasing familiarity and popularity in the hospital emergency room setting. The use of oxygen mask assemblies in emergency situations has proven advantageous because it avoids intubation and its associated risks of aspiration, infection, trauma, misplaced ET tubes, prolonged ventilation, and increased hospitalization and expenses. Moreover, the use of an oxygen mask assembly avoids the need for sedation, preserves speech and swallowing, improves oxygenation and decreases the physiologic work load on the heart.

U.S. Pat. No. 3,977,432 discloses one such oxygen mask assembly incorporating an oxygen dilutor including side wall apertures which allow for the entry of oxygen diluting air. A disadvantage associated with the assembly disclosed in U.S. Pat. No. 3,977,432 however is the tendency for the apertures in the dilutor side wall to become occluded when the dilutor contacts either the patient or the emergency personnel while the assembly is in use. Another disadvantage is that it does not incorporate any means for maintaining or adjusting continuous positive oxygen pressure.

It would thus be desirable to provide an oxygen mask assembly including, among other elements, an oxygen dilutor where the air inlet apertures are located thereon so that the risk of occlusion is minimized. It would also be desirable to provide a mask in which positive airway oxygen pressure can be maintained and adjusted. The present invention provides an oxygen mask assembly incorporating such an improved dilutor and mask.

SUMMARY OF THE INVENTION

An oxygen mask assembly embodying the present invention incorporating a dilutor with top wall apertures which minimize the risk of occlusion, a valve assembly for maintaining positive airway pressure, and a mask in which the pressure can be adjusted.

Particularly, the oxygen mask assembly includes a mask, a flexible hose having one end operatively connected to the mask, and an oxygen dilutor including an outlet connected to the opposite end of the hose and an oxygen inlet adapted for connection to an oxygen source. The dilutor includes an air inlet defined in a top wall thereof for diluting the oxygen flowing through the dilutor.

In one embodiment, the dilutor includes a head which includes the top wall and defines an interior cavity. The top wall includes an aperture and the dilutor further includes a rotatable port which covers the top wall of the head. The port includes an aperture adapted for rotatable alignment with the aperture in the top wall to define the air inlet. A jet extends unitarily outwardly from the top wall of the head. The jet defines the oxygen inlet and includes an interior conduit in fluid flow communication with the head cavity at one end and the oxygen source at the other end. A sleeve which extends upwardly from the top wall of the head surrounds the jet and is adapted for rotatable movement relative to the port and the jet. The sleeve includes a threaded inner surface which surrounds and is spaced from the jet and is adapted for threaded engagement with an oxygen supply hose.

In one embodiment, the oxygen mask assembly also includes an air reservoir bag assembly connected to the hose between the dilutor and the mask. The air bag assembly includes a connector with an interior surface defining a conduit having first and second inlet openings in fluid flow communication with and connected to the hose and a third opening in fluid flow communication with an air bag.

In the same embodiment, the oxygen mask assembly further includes a one-way inhalation valve assembly connected to the hose between the dilutor and the mask. The valve assembly includes a connector with an interior surface defining a conduit having first and second inlet openings in fluid flow communication with the hose and a third inlet opening in fluid flow communication with a one-way inhalation valve. The one-way valve assembly allows continuous positive airway pressure to be maintained in the mask.

Still further, in the same embodiment, the oxygen mask assembly includes a pressure valve assembly operably associated with and connected to the mask. The pressure valve assembly includes a body having an inlet in fluid flow communication with the interior of the mask and an outlet in fluid flow communication with the ambient air. The pressure valve assembly further includes a plunger covering the inlet, a cap threadingly secured to the top of the pressure valve assembly and a spring abutting the plunger and the cap respectively whereby the rotation of the cap results in the movement of the plunger towards or away from the inlet for adjusting the air pressure in the mask.

In one embodiment, the mask includes a frame with prongs thereon and a peripheral inflatable bladder which defines the face of the mask. The mask further includes a headband with straps having apertures therein adapted to receive the prongs on the frame for securing the headband to the mask.

BRIEF DESCRIPTION OF THE DRAWINGS

In the accompanying drawings forming part of the specification, in which like numerals are employed to designate like parts throughout the same.

FIG. 4 is a top plan view of the oxygen dilutor assembly of FIG. 2 with the top wall apertures therein in their closed orientation;

FIG. 5 is a top plan view of the oxygen dilutor assembly of FIG. 2 with the top wall apertures therein in their aligned orientation for maximum oxygen dilution;

FIG. 6 is an enlarged partly broken vertical cross-sectional view of the air reservoir bag assembly of the oxygen mask assembly of FIG. 1;

FIG. 7 is an enlarged partly broken vertical cross-sectional view of the inhalation one-way valve assembly of the oxygen mask assembly of FIG. 1;

FIG. 8 is a front elevational view of the inlet of the inhalation one-way valve assembly shown in FIG. 7;

DETAILED DESCRIPTION OF THE PREFERRED EMBODIMENTS

Figure 1:
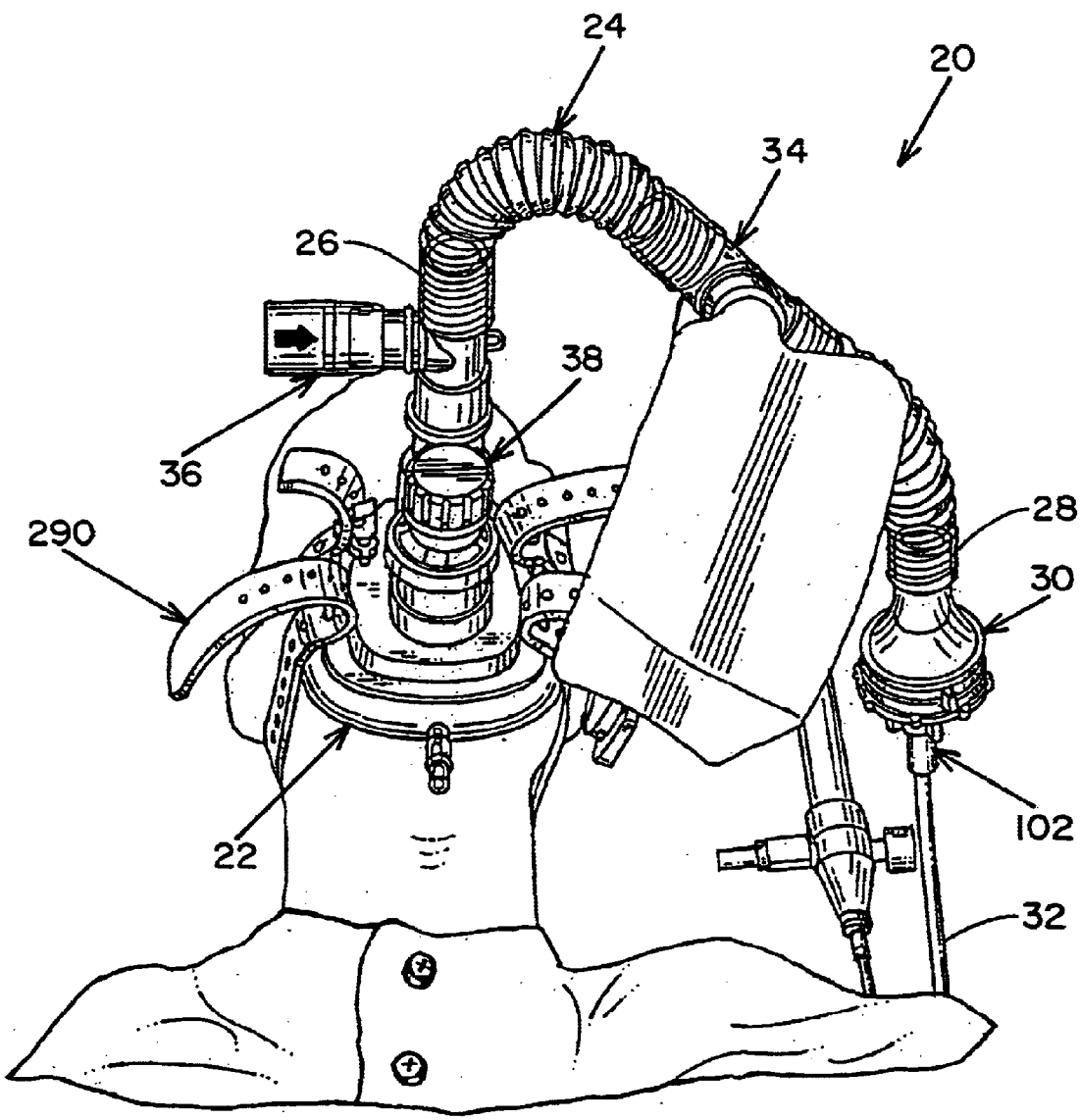
FIG. 1 is a perspective view of one embodiment of an oxygen mask assembly of the present invention, the assembly being depicted in use in an emergency setting.
Figure 2:
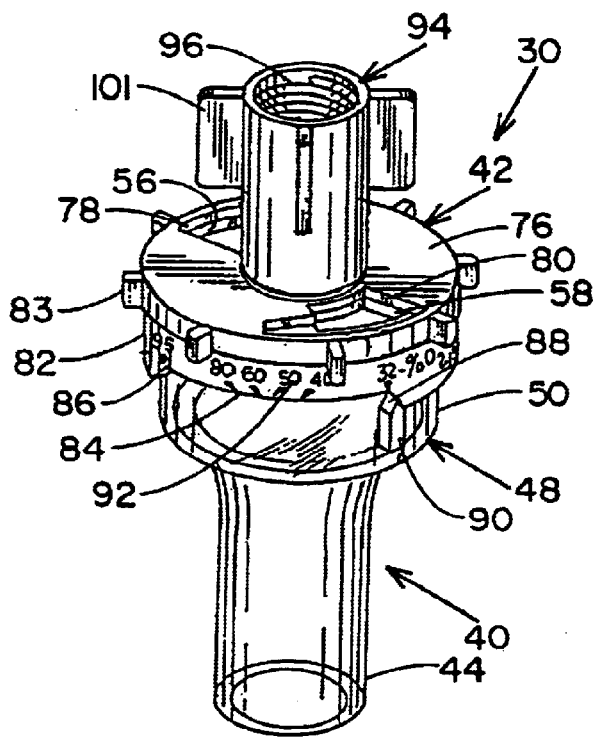
FIG. 2 is an enlarged perspective view of the oxygen dilutor assembly of the oxygen mask assembly of FIG. 1.

Referring to FIG. 1, an oxygen mask assembly 20 embodying the present invention includes an oxygen mask 22, a flexible respiratory circuit hose 24 having a proximal end 26 operably connected and extending into the mask 22 and a distal end 28 connected to and extending into an oxygen dilutor assembly 30 which is adapted for connection to an oxygen supply hose 32 which, in turn, is adapted for connection to an oxygen source (not shown).

The mask assembly 20 additionally includes an air reservoir bag assembly 34 connected to the respiratory circuit hose 24 between the oxygen dilutor assembly 30 and the mask 22, a one-way inhalation valve assembly 36 connected to the respiratory circuit hose 24 between the air reservoir bag assembly 34 and the mask 22, and an adjustable pressure valve assembly 38 operably associated with and connected to the top of the mask 22.

The invention disclosed herein is, of course, susceptible of embodiment in many different forms. Shown in the drawings and described hereinbelow in detail are two preferred embodiments of the invention. It is to be understood, however, that the present disclosure is an exemplification of the principles of the invention and does not limit the invention to the two illustrated embodiments.

For ease of description, the oxygen mask assembly 20 embodying the present invention is described hereinbelow in the position in which it is typically used as shown in the accompanying drawings and terms such as upper, lower, horizontal, etc., will be used herein with reference to this usual use position. It is understood, however, that the oxygen mask assembly may be manufactured, stored, transported, sold, or used in orientations other than those described and shown herein.

The oxygen dilutor assembly 30 is illustrated most clearly in FIGS. 2–5 and consists essentially of two parts, i.e., a flared body 40 and a port 42 which covers and is rotatably mounted to the top of the body 40. Each of the parts is preferably formed of a tough, semi-rigid material such as polypropylene or the like.

The body 40 additionally includes a stem or jet orifice 60 unitary with and extending generally perpendicularly upwardly from the top wall 52 of the head 48 in general co-linear relationship with the longitudinal axis of the body 40. The stem 60 includes a generally cylindrically shaped body 62 terminating in a radially inwardly extending shoulder 64, a generally cylindrically shaped collar 66 extending unitarily upwardly from the inner peripheral edge of the shoulder 64, a unitary shoulder 68 extending radially outwardly from the top of the collar 66 in spaced-apart and parallel relationship to the shoulder 64, and a generally rounded head 70 extending unitarily upwardly from the shoulder 68. The jet 60 additionally includes an interior longitudinal extending central bore 72 defining an oxygen conduit in fluid flow communication with the interior of the chamber 54 and terminating in an inlet 74 in the head 70.

The top wall 52 additionally includes one or more spaced-apart generally curvilinearly shaped apertures 56 and 58 adapted to allow the entry of diluting air into the chamber 54 as described below in more detail.

The body 40 additionally includes a stem or jet orifice 60 unitary with and extending generally upwardly from the top wall 52 of the head 48 in general co-linear relationship with the longitudinal axis of the body 40. The stem 60 includes a generally cylindrically shaped body 62 terminating in a radially inwardly extending shoulder 64, a generally cylindrically shaped collar 66 extending unitarily upwardly from the inner peripheral edge of the shoulder 64, a unitary shoulder 68 extending radially outwardly from the top of the collar 66 in spaced-apart and parallel relationship to the shoulder 64, and a generally rounded head 70 extending unitarily upwardly from the shoulder 68. The jet 60 additionally includes an interior longitudinal extending central bore 72 defining an oxygen conduit in fluid flow communication with the interior of the chamber 54 and terminating in an inlet 74 in the head 70.

The port 42 includes a generally flat radial top face or wall 76 (FIG. 2) which also includes one or more spaced-apart curvilinearly shaped apertures 78 and 80 and a circumferentially extending side wall 82 which depends and extends generally perpendicularly downwardly and unitarily from the peripheral outer edge of the face 76. A plurality of fingers 83 extend outwardly from and around the circumference of the side wall 82 in spaced-apart relationship.

The port 42 fits snugly but rotatably over the head 48 in a relationship where the face 76 of the port 42 abuts against the outer surface of the top wall 46 of the head 48 and the port side wall 82 surrounds and abuts against the top portion of the outer surface of the head side wall 50.

The port apertures 78 and 80 are positioned and dimensioned to be brought into either complete, partial, or no alignment with the respective apertures 56 and 58 in the top wall 52 of the head 48 in response to the rotation of the port 42 relative to the head 48 as explained in more detail below.

An elongate notch 84 is formed in, and extends a predetermined length along, the bottom peripheral edge of the port side wall 82. The notch 84 includes opposed shoulders or steps 86 and 88 which cooperate and engage with a tab 90 formed on the side wall 50 of the head 48 to limit the amount which the port 42 rotates relative to the head 48 and define the range of registration and alignment between the apertures in the head 48 and the port 42 respectively.

The tab 90 additionally forms an indicator arrow or pointer adapted for alignment with numerals or other suitable indicia 92 which are formed or otherwise permanently affixed to the outer surface of the port side wall 82 above the notch 84 thereof and which represent the oxygen concentration at each of the predetermined settings. In the depicted embodiment of the present invention, the apertures in the head 48 and the port 42 have been sized respectively to allow the selection of oxygen dilution levels between the 32% oxygen level shown in FIGS. 2 and 5 where the port 42 is open and respective apertures are in complete registry with each other for maximum oxygen dilution and the 100% oxygen level shown in FIG. 5 where the port 42 is closed and the apertures in the port 42 and the head 48 respectively are not aligned.

The dilutor assembly 30 additionally includes a sleeve 94 which is integral with, and extends upwardly centrally from, the radial face 76 of the port 42 and surrounds the jet 60. The sleeve 94 is aligned generally co-linearly with the longitudinal axis of the body 40 and includes a cylindrically shaped and threaded inner surface 96 which surrounds and is spaced from the jet 60. A hook-shaped finger 98 extends circumferentially and unitarily outwardly from the sleeve inner surface 96 to define an inner circumferentially extending radial groove 100. The circumferential finger 98 is fitted in the collar 66 of the jet 60 between the shoulders 64 and 66 thereby mounting the sleeve 94 for rotational movement relative to, and independent of, the jet 60 and the port 42. A plurality of fins 101 extend around the outer surface of the sleeve 94 in a spaced-apart and general vertical relationship.

Figure 3:
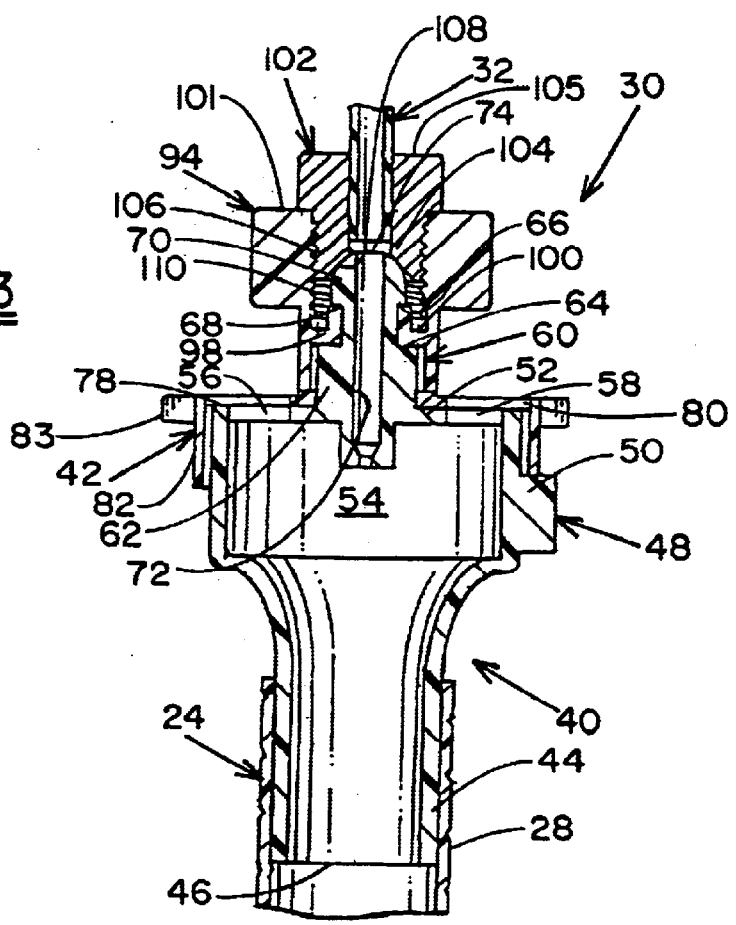
FIG. 3 is an enlarged partly broken vertical cross-sectional view of the oxygen dilutor assembly shown connected to the oxygen supply hose at one end and the circuit hose at the other end.
Figure 9:
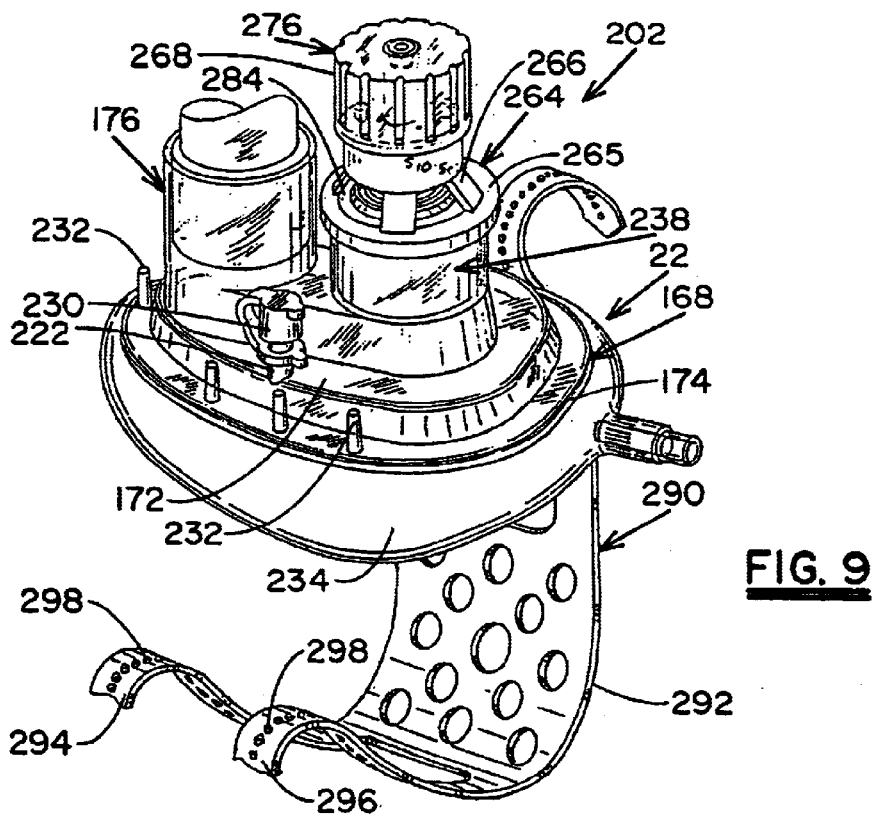
FIG. 9 is a partly broken perspective view of the mask and the headband of the oxygen mask assembly of FIG. 1.
Figure 10:
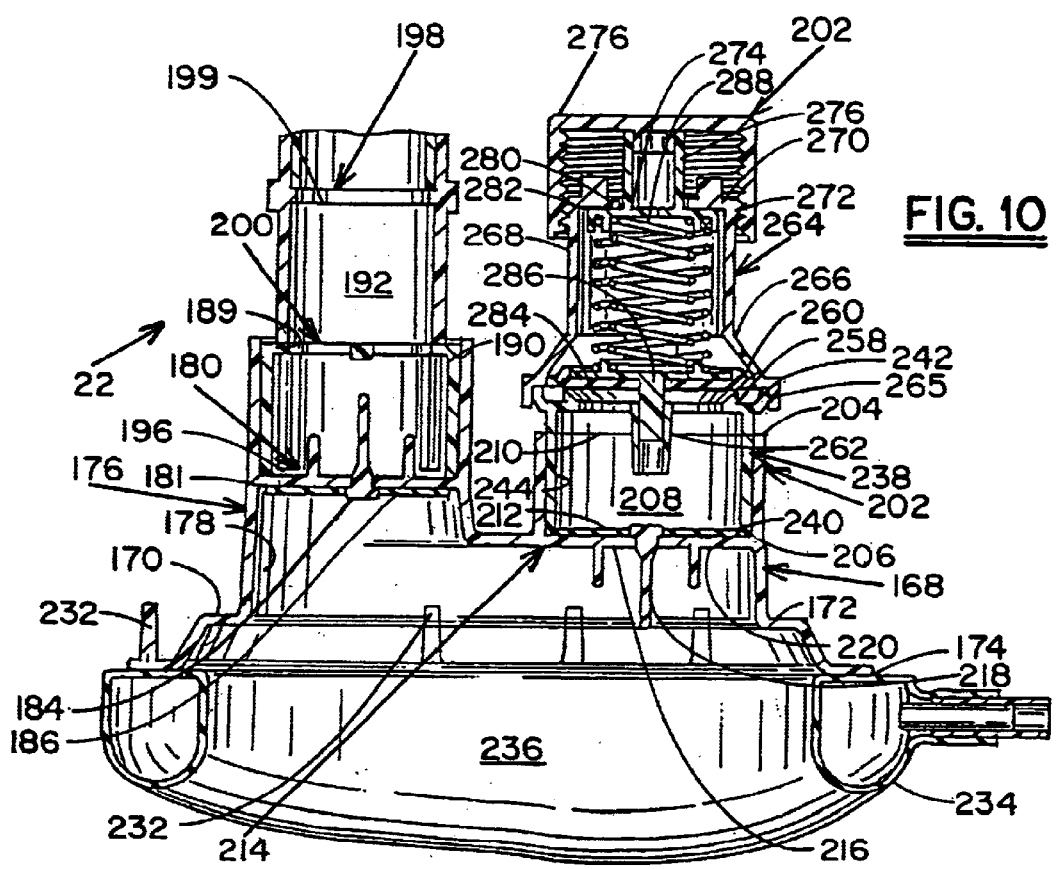
FIG. 10 is a vertical cross-sectional view of the mask of FIG. 9.
Figure 11:
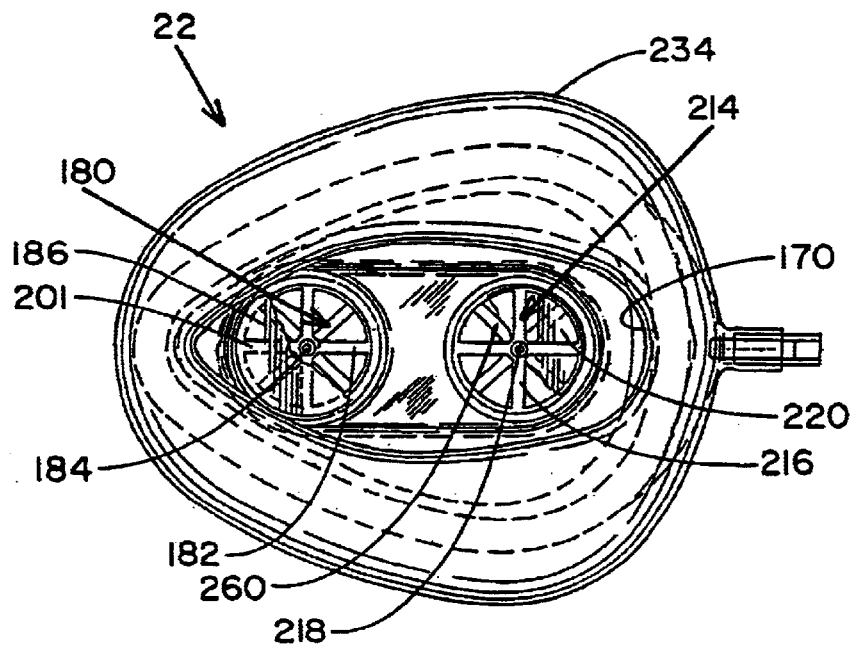
FIG. 11 is a bottom plan view of the mask of FIG. 9.

Referring to FIGS. 1 and 3, the oxygen supply hose 32 includes a tip 102 which is threadingly securable to the end of the sleeve 94. Particularly, the tip 102 includes a shouldered collar 105 which abuts against the distal end of the sleeve 94 and a generally cylindrically shaped plug 104 which extends unitary outwardly from the collar 105 and is sized to fit into the end of the sleeve 94. The plug 104 includes a threaded outer surface 106 adapted for threading engagement with the threaded sleeve inner surface 96. The plug 104 additionally includes an interior cavity 108 extending into the distal end thereof which is shaped and sized to receive the rounded head 70 of the jet 60 as shown in FIG. 3 when the tip 102 is secured to the sleeve 94. The cavity 108 additionally forms a peripheral radial collar 110 at the end of the plug 104 which fits into the radial groove 100 in the inner surface 96 of the sleeve 94. The tip 102, like the dilutor 30, is also made of a tough, semi-rigid material such as polypropylene or the like.

Referring to FIGS. 1 and 6, the air reservoir bag assembly 34 includes a connector 112 which, in the embodiment shown, is in the shape of a "T" including respective ends 114, 116 and 118 and an interior generally cylindrical surface defining an interior "T" shaped cavity 120 and respective inlet openings 122, 124 and 126 in the ends 114, 116 and 118 respectively. The ends 114 and 116 and the inlet openings 122 and 124 oppose each other in a generally co-linear relationship and are connected to and in fluid communication with the circuit hose 24. The end 118 is disposed generally between and normal to the ends 114 and 116. The inlet opening 126 therein is in fluid flow communication with the inlet openings 122 and 124 and the hose 24 via the cavity 120. An air bag 128, which can be made of a soft, flexible and inflatable plastic or the like material, is connected to the conduit end 118 and is in fluid flow communication with the inlet opening 126 therein. The connector 112 is also made of a tough, semi-rigid material such as polypropylene or the like.

Referring to FIGS. 1, 7 and 8, the inhalation one-way valve assembly 36 also includes a connector 130 made of the same type of material as the connector 112 which, in the embodiment shown, is also in the shape of a "T" and includes respective opposed ends 132 and 134 which are connected respectively to the hose 24 and the mask 22 (via a coupling 138) and an end 136 therebetween to which a one-way valve 140 is connected. The connector 130 includes a generally cylindrical interior surface defining a "T" shaped cavity 142 and inlet openings 144, 146 and 148 formed in the ends 132, 134 and 136 respectively. The ends 132 and 134 and the inlet openings 144 and 146 respectively oppose each other in a generally co-linear relationship and are connected to, and in fluid flow communication with, the hose 24 and the mask 22 respectively. The end 136 is disposed generally normal and between the ends 132 and 134 and inlet opening 148 therein is in fluid flow communication with the inlet openings 144 and 146 via the cavity 142.

The valve 140 includes opposed ends 152 and 154, is generally cylindrically shaped and includes a generally cylindrically shaped interior surface defining a bore 156 and respective inlet openings 158 and 160. The end 154 is fitted over the end 136 of the connector 130 in a relationship wherein the opening 160 in the valve 150 is in fluid flow communication with the opening 148 in the connector 130. A unitary screen 162 defined by cross-bars 164 extends radially across the bore 156 between opposed sides of the interior surface thereof generally mid-way between the respective ends 152 and 154 of the valve 140. A pin 164 extending through the center of the screen 162 secures a sponge-like circular filter 166 against one of the sides of the screen 162.

The mask 22 shown in FIGS. 1 and 9–11 is formed of a resilient plastic material and includes a frame or body 168 configured and shaped to fit over the mouth and the nose of a patient. The body 168 includes an inner surface 170, an upper or top surface 172 and an outer peripheral edge 174. A generally cylindrically shaped oxygen inlet conduit 176 extends unitarily outwardly from the top surface 172. The conduit 176 includes a generally cylindrically shaped interior surface defining an interior bore 178 and respective openings 179 and 181 in fluid flow communication with the coupling 138 and the mask inner surface 170 respectively. A unitary screen 180 defined by cross-bars 182 extends radially across the bore 178 between opposed sides of the conduit interior surface. A pin 184 extending through the center of the screen 180 secures a sponge-like circular filter 186 against the lower side of the screen 180.

The coupling 138 is generally cylindrically shaped and includes opposed ends 188 (FIG. 7) and 190 and a cylindrically shaped inner surface defining a bore 192 and opposed openings 194 (FIG. 7) and 196 in the ends 188 and 190 respectively. Unitary screens 198 and 200 defined by cross-bars 199 and 201 respectively extend radially across the bore 192 between opposed sides of the conduit interior surface in spaced-apart and parallel relationship.

Coupling 138 is connected and secured to the mask conduit 176 in a relationship where the end 190 thereof is in abutting relationship with the upper surface of the screen 180 therein and the end 134 of the connector 130 of the one-way valve assembly 36 is connected and secured inside the end 188 of the coupling 138 in a relationship where the connector end 134 is in abutting relationship with the upper surface of the screen 198 (FIG. 7).

The mask 22 additionally includes a generally cylindrically shaped pressure outlet conduit 202 which extends unitarily upwardly from the top surface 172 in a generally opposed and co-linear relationship with, and relative to, the conduit 176. The conduit 202 includes opposed ends 204 and 206 and a generally cylindrically shaped interior surface defining an interior bore 208 and openings 210 and 212 in fluid flow communication with the exhalation pressure valve assembly 38 and the mask interior surface 170 respectively.

A unitary screen 214 defined by cross-bars 216 extends radially across the bore 208 between opposed sides of the conduit interior surface and adjacent the opening 212. A pin 218 extending through the center of the screen 214 secures a sponge-like circular filter 220 against the upper side of the screen 214.

The mask 22 further includes an oxygen outlet valve 222 (FIG. 9) also extending unitarily outwardly from the mask top surface 172 in a generally spaced-apart relationship to the conduits 176 and 202 respectively. The valve 222 includes a generally cylindrically shaped interior surface which defines an interior longitudinal bore (not shown) and respective openings (not shown) in fluid flow communication with the ambient air and the mask interior surface 170 respectively. A removable cap 230 plugs the valve 222.

The mask 22 further includes a plurality of spaced-apart, co-linearly aligned dowel-shaped prongs or projections 232 located on opposite sides of the body 168 and extending unitarily outwardly from the upper surface 172 thereof along peripheral edge 174 thereof.

A bladder 234, which is formed of a soft inflatable plastic or the like material, is connected to and extends outwardly from and around the mask's peripheral edge 174. The bladder 234 is countered and shaped to be rested against the patient's face and to surround the patient's mouth and nose. The bladder 234 together with the mask interior surface 170 define an oxygen inhalation chamber 236.

The pressure valve assembly 38 includes a generally cylindrically shaped hollow body 238 having opposite ends 240 and 242 and a generally cylindrical interior surface defining a chamber or bore 244 and openings in the ends 240 and 242 respectively. A screen 258 defined by cross-bars 260 extends unitarily radially across the bore 244 between opposed sides of the bore interior surface and adjacent the end 242. A hollow neck 262 is formed and positioned centrally on the screen 258 and extends unitarily downwardly from the center thereof into the bore 244 of the body 238. The body 238 is fitted into the interior of the mask conduit 202 in a relationship where the end 240 thereof abuts against the upper peripheral edge of the screen 214.

The pressure valve assembly 38 additionally includes a head 264 secured to the top of the body 238. The head 264 includes a ring 265 which is fitted over the top peripheral edge of the end 242 of the body 238, a plurality of ribs 266 converging unitarily upwardly from the top of the ring 265 in a spaced-apart and circumferential relationship, and a generally cylindrically shaped hollow chamber 268 extending unitarily upwardly from the upper ends of the ribs 266. The chamber 268 terminates in a flange 270 which extends radially inwardly from a threaded peripheral upper edge 272 thereof and defines a central generally circular opening 274 in the top of the chamber 268. A cap 276 is threadingly secured to the top of the chamber 268 and includes a sleeve 276 which extends longitudinally unitarily downwardly from the interior bottom surface of the cap 276 into and through the opening 274 in the head 264. The sleeve 276 terminates in a radially outwardly extending flange 280 which includes a peripheral circumferential extending slot 282 and an upper surface which abuts against the lower surface of the flange 270 of the head 264.

A generally circular plunger 284, made of rubber or the like material, is seated against the screen 258 and blocks the opening 248 in the body 238. The plunger 284 includes a central unitary shaft 286 which extends through the neck 262 of the screen 258. A coil-type spring 288 located inside the head 264 has one end abutted against the top of the plunger 284 and an opposed end fitted into the slot 282 in the cap 276.

The mask assembly 20 additionally includes a flexible plastic headband 290 (FIGS. 1 and 9) having an expanded head portion 292 adapted to be placed against the back of the patient's head and flexible elongate straps 294 and 296 extending unitarily outwardly from opposite sides of the head portion 292 in spaced-apart relationship. Each of the straps 294 and 296 includes a plurality of spaced-apart apertures 298.

The oxygen mask assembly 20 of the present invention is adapted for use in, for example, an ambulance or in a hospital emergency room, where rapid response to, for example, cardiopulmonary trauma is necessary and crucial.

The securement of the mask 22 over the mouth and the nose of the patient as shown in FIG. 1 is quickly and easily accomplished simply by wrapping the headband 290 around the head of the patient and strapping the straps 294 and 296 and, more particularly respective ones of the apertures 298 therein, to respective ones of the prongs 232 on opposite sides of the mask 22.

The connection of the mask assembly 20 to an oxygen source is also quickly and easily accomplished simply by grasping the fins 101 on the sleeve 94 and threading the tip 102 of the oxygen supply hose 32 into the end of the oxygen dilutor assembly 30.

With the mask 22 firmly secured to the patient and the assembly 20 connected to the oxygen source, the paramedic or other emergency health care personnel is next able to quickly and easily set and/or subsequently adjust the oxygen concentration by rotating the port 42 at the top of dilutor assembly 30 to the desired oxygen concentration level. The placement of the dilutor apertures in the top wall of the dilutor 30, instead of the side wall as in other available dilutors, eliminates the risk of aperture occlusion from contact with the patient or the emergency personnel.

The continuous positive airway pressure in the mask 22 can also be quickly and easily set and/or subsequently adjusted simply by rotating the cap 276 on the top of the mask 22 to the desired pressure setting between five (5) and twenty (20) centimeters water pressure. In accordance with the present invention, the rotation of the cap 276 causes either the compression or the expansion of the spring 288 in the valve assembly 38 which in turn causes the movement of the plunger 284 either towards or away from the opening 248 to respectively either release or increase the pressure in the pressure chamber 240 and the mask interior in fluid flow communication therewith.

According to the invention, continuous positive mask pressure is generated by the patient and is maintained by the one-way valve assembly 36 which, upon inhalation, allows oxygen to flow from and through the dilutor assembly 36 into the mask 22. In the event of oxygen flow failure or hose occlusion, the valve 222 can be quickly and easily uncapped to allow the partial breathing of ambient air.

Figure 12:
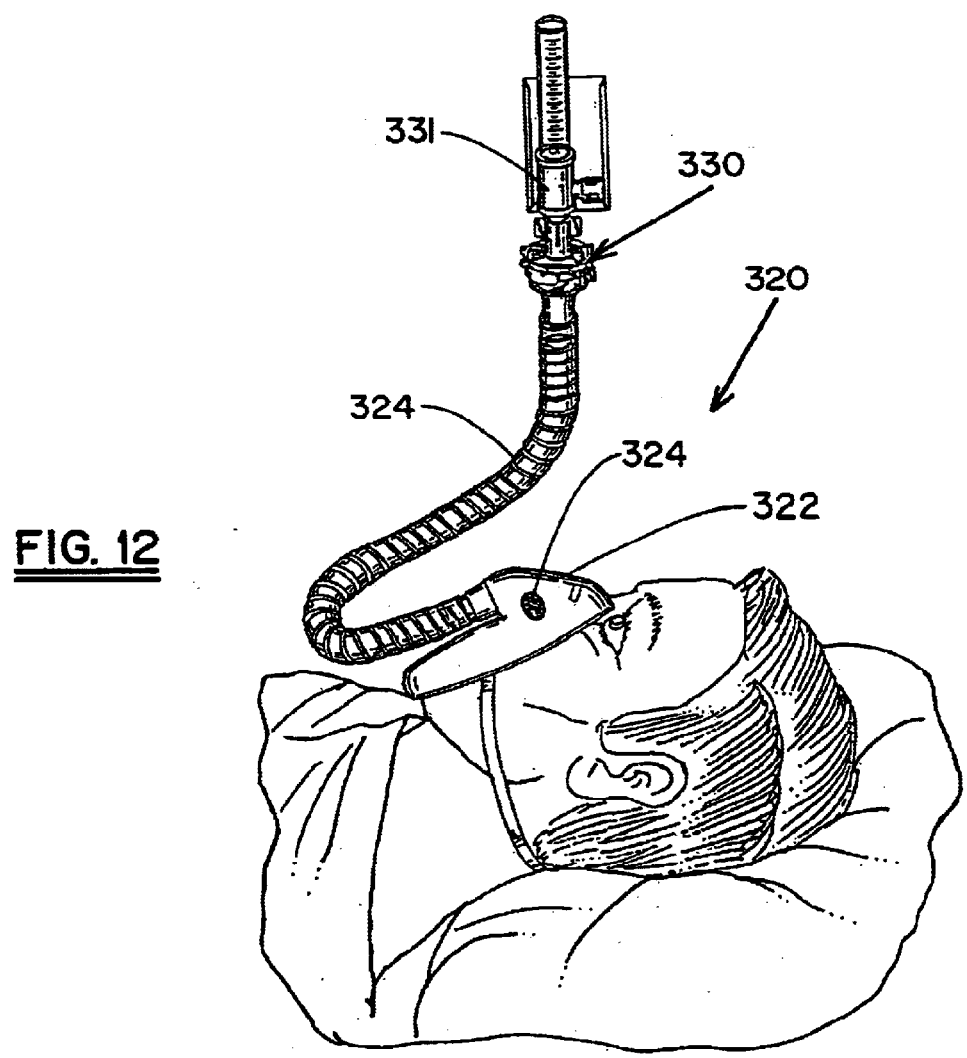
FIG. 12 is a perspective view of an alternate embodiment of the oxygen mask assembly of the present invention in use in a hospital emergency room setting.

FIG. 12 depicts an alternate oxygen mask assembly 320 which is adapted for use in a hospital room setting and includes a respiratory circuit hose 324 and an dilutor assembly 330 similar in structure to the hose 24 and the dilutor assembly 30 of the oxygen mask assembly 20. The dilutor assembly 320 is shown connected to a hospital room oxygen supply feed 331 which includes a threaded tip (not shown) similar in structure to the tip 102 of the oxygen hose 32 described earlier. The assembly 320 differs in structure from the assembly 20 in that it incorporates a non-pressurized mask 322 with air vents 324 formed in the outer surface thereof. Because the mask 322 is not pressurized, the assembly 330 does not need, and thus does not include, either a reservoir bag assembly or a one-way valve assembly as in the assembly 20. As a result, oxygen flows continuously with no change in applied pressure through the dilutor 330, the hose 334 and into the vented mask 222.

The foregoing specification and drawings are to be taken as illustrative but not limiting of the present invention. Still other mask and oxygen dilutor assemblies utilizing the spirit and scope of the present invention are possible, and will readily present themselves to those skilled in the art.

We claim:

1. An oxygen mask assembly comprising;

a mask including a body defining an interior;

a flexible hose having one end operatively connected to said mask; and an oxygen dilutor including an outlet connected to the opposite end of said hose and an oxygen inlet adapted for connection to an oxygen source and extending generally perpendicularly outwardly from a top wall of said oxygen dilutor, said dilutor including an air inlet defined in the top wall including said oxygen inlet for diluting the oxygen flowing through said dilutor, said dilutor including a head having said top wall and defining an interior cavity, said top wall including an aperture therein, said dilutor further including a rotatable port covering said top wall of said head, said port including an aperture adapted for rotatable alignment with said aperture in said top wall to define said air inlet.

2. The oxygen mask assembly of claim 1 further comprising an air reservoir bag assembly connected to said hose between said dilutor and said mask, said air bag assembly including a connector with an interior surface defining a conduit having first and second inlet openings in fluid flow communication with and connected to said hose and a third opening in fluid flow communication with an air bag.

3. The oxygen mask assembly of claim 1 further comprising an inhalation valve assembly connected to said hose between said dilutor and said mask, said valve assembly including a connector with an interior surface defining a conduit having first and second inlet openings in fluid flow communication with said hose and a third inlet opening in fluid flow communication with a valve.

4. The oxygen mask assembly of claim 1 further comprising a pressure valve assembly operably associated with and connected to said mask.

5. The oxygen mask assembly of claim 1 wherein said mask includes a frame having spaced-apart prongs extending outwardly from the top thereof, said mask further including a headband with straps having apertures therein adapted to be received in said prongs for securing said headband to said mask.

6. An oxygen mask assembly comprising:
a mask including a body defining an interior;
a flexible hose having one end operatively connected to said mask;
an oxygen dilutor including an outlet at a first end connected to the opposite end of said hose and an oxygen inlet at an opposite second end adapted for connection to an oxygen source and extending generally perpendicularly outwardly from a top wall of said oxygen dilutor, said dilutor including an air inlet defined in the top wall thereof including said oxygen inlet for diluting the oxygen flowing through said dilutor; and
a jet extending unitarily outwardly from said top wall of said head which defined said oxygen inlet and includes an interior conduit in fluid flow communication with said cavity in said head at one end and said oxygen source at the other end, said jet additionally including a sleeve extending upwardly therefrom and surrounding said jet for rotatable movement relative to said port and said jet, said sleeve including a threaded inner surface surrounding and spaced from said jet and adapted for threaded engagement with an oxygen supply hose.

7. An oxygen mask assembly comprising:
a mask including a body defining an interior;
a flexible hose having one end operatively connected to said mask; and an oxygen dilutor including an outlet connected to the opposite end of said hose and an oxygen inlet adapted for connection to an oxygen source and extending generally perpendicular outwardly from a top wall of said oxygen dilutor, said dilutor including an air inlet defined in the top wall including said oxygen inlet for diluting the oxygen flowing through said dilutor; and a pressure valve assembly operably associated with and connected to said mask, said pressure valve assembly including a body having an interior chamber defining an inlet in fluid flow communication with the interior of said mask and an outlet in fluid flow communication with the ambient air, said pressure valve assembly further including a plunger covering said inlet, a cap threadingly secured to the top of said pressure valve assembly and a spring abutting said plunger and said cap respectively whereby the rotation of said cap results in the movement of said plunger towards or away from said inlet for adjusting the air pressure in said mask.

8. An oxygen mask assembly comprising:
a mask including a frame defining an interior;
a flexible circuit hose having one end operably connected to said mask; and
an oxygen dilutor assembly including a top wall defining an air inlet aperture and an oxygen inlet jet extending generally perpendicularly outwardly from said top wall defining said air inlet aperture and adapted for connection to an oxygen source, said dilutor assembly further including an outlet extending into the opposite end of said circuit hose, said dilutor assembly including a head and a top wall together defining an interior chamber in fluid flow communication with said oxygen source, said top wall including an aperture defining an inlet adapted to allow the entry of ambient air into said chamber for diluting the oxygen in said chamber, said dilutor assembly further including a port covering said top wall and including an aperture therein, said port being rotatable relative to said head for bringing said apertures in said top wall of said head and said port respectively into registry to allow the entry of ambient air into said chamber.

9. The oxygen mask assembly of claim 8 wherein said port additionally includes a sleeve extending upwardly therefrom and surrounding said jet for rotatable movement relative to said port and said jet, said sleeve including a threaded inner surface surrounding and spaced from said jet and adapted for threaded engagement to an oxygen supply hose.

10. The oxygen mask assembly of claim 8 wherein said air bag assembly includes a generally T-shaped connector with an interior surface defining a conduit with first and second opposed inlet openings connected to and in fluid communication with said hose and a third inlet opening in fluid flow communication with said first and second opposed inlet openings and having an air bag connected thereto.

11. The oxygen mask assembly of claim 8 wherein said inhalation valve assembly includes a generally T-shaped connector having an interior surface defining a conduit with first and second opposed inlet openings operably connected to and in fluid communication with said hose and said mask respectively and a third inlet opening in fluid flow communication with said first and second opposed inlet openings and having a valve connected thereto.

12. The oxygen mask assembly of claim 8 wherein said pressure valve assembly includes an interior chamber defining an inlet in fluid flow communication with the interior of said mask and an outlet in fluid flow communication with the ambient air, said pressure valve assembly further including a head covering said pressure chamber, a plunger in said head covering said inlet, a cap threadingly secured to said top of said head and a spring in said head abutting said plunger and said cap respectively whereby the rotation of said cap relative to said results in the movement of said plunger towards or away from said inlet and the adjustment of the air pressure in said mask.

13. An oxygen dilutor assembly for use in an oxygen mask assembly, the oxygen dilutor assembly comprising:
   a head defining an interior cavity and including a top wall having an air aperture therein and an oxygen inlet jet in fluid flow communication with said interior cavity, said oxygen inlet jet extending outwardly from said top wall including said air aperture;
   a port rotatably secured to said top wall and including an aperture therein adapted for alignment with said air aperture in said top wall of said head to allow the entry of oxygen diluting air into said cavity, said port further including a sleeve rotatably secured to and surrounding and spaced from said jet and including a threaded inner surface; and
   an oxygen inlet hose including a plug adapted to be fitted over said jet and threadingly secured to said inner surface of said sleeve.

14. An oxygen dilutor assembly for use in an oxygen mask assembly, the oxygen dilutor assembly comprising:
   a head defining an interior cavity and including a top wall having an aperture therein and an oxygen inlet jet in fluid flow communication with said interior cavity and extending generally outwardly from said top wall, said jet including a collar;
   a port rotatably secured to said top wall and including an aperture therein adapted for alignment with said aperture in said top wall of said head to allow the entry of oxygen diluting air into said cavity, said port further including a sleeve rotatably secured to and spaced from said jet and including a threaded inner surface and a hook-shaped finger extending circumferentially and unitarily outwardly from the threaded inner surface of said sleeve and between the sleeve and the jet defining a groove and fitting into and surrounding said collar; and
   an oxygen inlet hose including a plug adapted to be fitted over said jet and including an interior cavity defining a circumferentially extending radial collar which is fitted in said groove in said sleeve when said plug is threadingly secured to said sleeve.

15. An oxygen dilutor assembly for use in an oxygen mask assembly, the oxygen dilutor assembly comprising:
   a head defining an interior cavity and including a top wall having an air aperture therein and an oxygen inlet jet in fluid flow communication with said interior cavity and extending generally outwardly from said top wall, said jet including a collar;
   a port rotatably secured to said top wall and including an aperture therein adapted for alignment with said air aperture in said top wall of said head to allow the entry of oxygen diluting air into said cavity, said port further including a sleeve rotatably secured to and spaced from said jet and including a threaded inner surface and a hook-shaped finger extending circumferentially and unitarily outwardly from the threaded inner surface of said sleeve and between the sleeve and the jet defining a groove and fitting into and surrounding said collar, said port further including a side wall surrounding said head and a notch extending along a portion thereof including opposed shoulders which cooperate and engage with a tab on the head to limit the amount which said port rotates relative to said head; and
   an oxygen inlet hose including a plug adapted to be fitted over said jet and including an interior cavity defining a circumferentially extending radial collar which is fitted in said groove in said sleeve when said plug is threadingly secured to said sleeve.

16. An oxygen mask assembly comprising;
   a mask;
   a flexible hose having one end operatively connected to said mask; and
   an oxygen dilutor including an outlet connected to the opposite end of said hose and an oxygen inlet jet including a collar and adapted for connection to an oxygen inlet hose including a plug, said dilutor including an air inlet defined in a top wall thereof for diluting the oxygen flowing through said dilutor and a sleeve rotatably secured to and surrounding and spaced from said jet, said sleeve including a finger which fits into and surrounds said collar, said finger further defining a groove, said plug defining a radial collar which is fitted in said groove in said sleeve when said plug is threadingly secured to said sleeve.

17. The oxygen mask assembly of claim 16 wherein said dilutor includes a head defining an interior cavity and said top wall.

18. The oxygen mask assembly of claim 16 wherein said dilutor includes a head having said top wall and defining an interior cavity, said top wall including an aperture therein, said dilutor further including a rotatable port covering said top wall of said head, said port including an aperture adapted for rotatable alignment with said aperture in said top wall to define said air inlet.

19. The oxygen mask assembly of claim 16 further comprising an air reservoir bag assembly connected to said hose between said dilutor and said mask, said air bag assembly including a connector with an interior surface defining a conduit having first and second inlet openings in fluid flow communication with and connected to said hose and a third opening in fluid flow communication with an air bag.

20. The oxygen mask assembly of claim 16 further comprising an inhalation valve assembly connected to said hose between said dilutor and said mask, said valve assembly including a connector with an interior surface defining a conduit having first and second inlet openings in fluid flow communication with said hose and a third inlet opening in fluid flow communication with a valve.

21. The oxygen mask assembly of claim 16 further comprising a pressure valve assembly operably associated with and connected to said mask.

22. The oxygen mask assembly of claim 21 wherein said pressure valve assembly includes a body having an interior chamber defining an inlet in fluid flow communication with the interior of said mask and an outlet in fluid flow communication with the ambient air, said pressure valve assembly further including a plunger covering said inlet, a cap threadingly secured to the top of said pressure valve assembly and a spring abutting said plunger and said cap respectively whereby the rotation of said cap results in the movement of said plunger towards or away from said inlet for adjusting the air pressure in said mask.

23. The oxygen mask assembly of claim 16 wherein said mask includes a frame and a peripheral inflatable bladder defining the face of said mask.

24. The oxygen mask assembly of claim 16 wherein said mask includes a frame having spaced-apart prongs extending outwardly from the top thereof, said mask further including a headband with straps having apertures therein adapted to be received in said prongs for securing said headband to said mask.

* * * * *